(12) United States Patent
Nance

(10) Patent No.: US 6,638,064 B1
(45) Date of Patent: Oct. 28, 2003

(54) FLEXIBLE ENDODONTIC SYRINGE

(76) Inventor: Robert Scott Nance, 1701 Davie Ave., Statesville, NC (US) 28677

( * ) Notice: Subject to any disclaimer, the term of this patent is extended or adjusted under 35 U.S.C. 154(b) by 366 days.

(21) Appl. No.: 09/588,981

(22) Filed: Jun. 7, 2000

(51) Int. Cl.$^7$ .................................................. A61C 5/02
(52) U.S. Cl. ........................................................ 433/81
(58) Field of Search ............................. 433/80, 81, 82, 433/102, 224

(56) References Cited

U.S. PATENT DOCUMENTS

| | | |
|---|---|---|
| 3,745,655 A | 7/1973 | Malmin |
| 3,807,048 A | 4/1974 | Malmin |
| 3,816,921 A | 6/1974 | Malmin |
| 4,276,880 A * | 7/1981 | Malmin ................ 433/80 |
| 4,472,141 A | 9/1984 | Dragan |
| 5,000,912 A | 3/1991 | Bendel et al. |
| 5,540,587 A * | 7/1996 | Malmin ................ 433/81 |
| 5,605,460 A | 2/1997 | Heath et al. |
| 5,713,736 A | 2/1998 | Heath et al. |
| 5,713,910 A | 2/1998 | Gordon et al. |
| 5,861,002 A | 1/1999 | Desai |
| 5,893,713 A | 4/1999 | Garman et al. |
| 5,935,096 A | 8/1999 | Barrett |
| 5,989,209 A | 11/1999 | Barrett |
| 6,079,979 A * | 6/2000 | Riitano ................ 433/81 |

FOREIGN PATENT DOCUMENTS

WO    WO 96/38594 A1    12/1996

* cited by examiner

Primary Examiner—Nicholas D. Lucchesi
(74) Attorney, Agent, or Firm—Summa & Allan, P.A.

(57) ABSTRACT

A flexible endodontic syringe for use in performing root canal therapy on a tooth and that is particularly useful for irrigating a root canal possessing a non-linear central axis is presented. The instrument comprises an elongate shank or needle having an enclosed axial channel or lumen. The shank or needle possesses a flexibility sufficient to substantially traverse the entire length of a root canal. A method for irrigating a root canal is also disclosed.

31 Claims, 5 Drawing Sheets

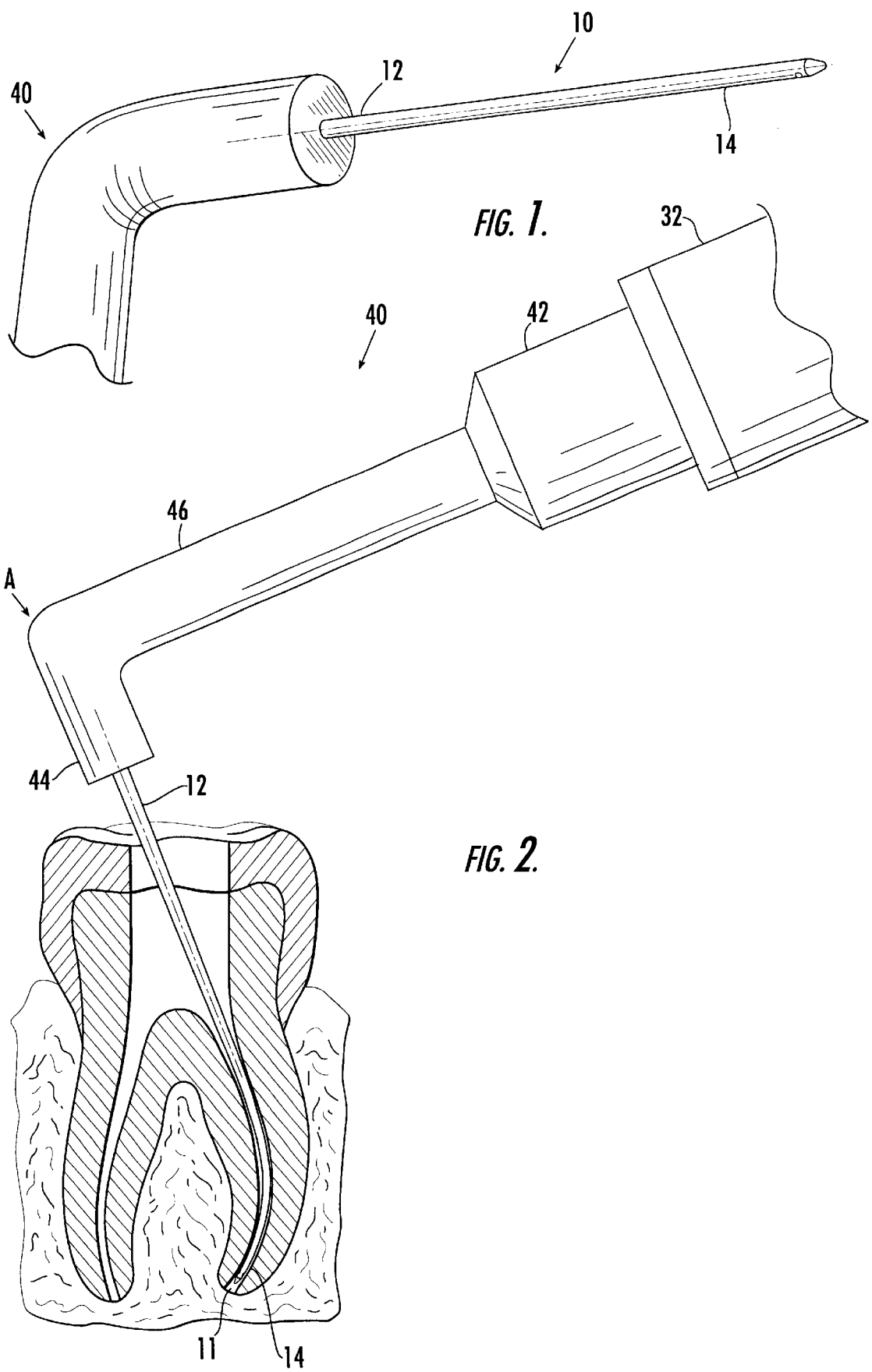

FLEXIBLE ENDODONTIC SYRINGE

FIELD OF THE INVENTION

The invention is an apparatus and method for use in dental applications. In particular, the invention is an apparatus and method for use in endodontic or root canal procedures.

BACKGROUND

Endodontics or root canal therapy is a well-known dental procedure wherein the crown of a diseased tooth is opened to permit the canal (or canals) of the tooth to be cleaned and filled. In general terms, a root canal proceeds as follows. The crown of the tooth is opened to expose the root canal. Typical root canals have a non-linear central axis, i.e., they are curved, and the curve of the canal can be quite severe. During an endodontic procedure, a series of very delicate, flexible, rotary driven or finger-held instruments or files are used to extirpate or clean out and shape the root canal. These files typically possess contoured or rough outer surfaces to enable the endodontist to break up and loosen tissue as well as remove infected dentin from the canal walls within the root canal. Examples of such files are discussed in U.S. Pat. No. 5,713,736 to Heath et al. The endodontist usually rotates and reciprocates the file to bring loose tissue and debris out of the root canal.

The files, however, are incapable of removing all of the necessary tissue and debris, especially tissue and debris trapped in the smaller lateral canals extending off the main canal. Thus, Endodontists remove this tissue and debris by injecting a fluid (typically a disinfecting agent or chelating agent) into the canal to irrigate the canal. The typical disinfecting fluid is a dilute solution of sodium hypochlorite. Ethylenediaminetetraacetic acid (EDTA) is a typical chelating agent.

Fluid injection is accomplished by means of a hollow needle or syringe. As used herein, the term needle will generally refer to the elongate, typically metal shank traditionally associated with medical injections. The term needle and shank may be used interchangeably herein unless the context of the description or claims requires otherwise. The term syringe is used to encompass both a needle and other elements necessary to discharge a fluid from a needle such as a fluid reservoir and plunger. The injection and removal of the solution is referred to as "irrigating" or "aspirating" the canal.

After irrigation, the cleaned, disinfected and vacant root canal is then obturated or filled, typically with a waxy, rubbery compound known as gutta percha. A set of rod-like pluggers similar to the files used to extirpate the canal force the gutta percha down into the canal. After the canal is filled, the crown of the tooth is repaired thereby completing the procedure.

The non-linear structure of root canals presents several problems for endodontists. The canal must be cleaned and disinfected but the integrity of the canal must be maintained. If a stiff file or plugger is used, the distal end of the tool may pierce the sidewall of the canal and destroy the tooth. If a flexible file or plugger is used, it must maintain enough rigidity to accomplish the task of removing or inserting material. For many years, a suitable material for making files and pluggers did not exist and endodontists compensated by creating larger entry holes in crowns and using the best materials at hand.

In the late 1980's and early 1990's, nickel-titanium alloys possessing superelastic and suitable shape memory properties became available. Instrument companies began manufacturing files and pluggers made from these alloys. The nickel-titanium files and pluggers allowed the endodontist to reach the bottom of the root canal without excessive risk of puncturing the side of the canal.

Although nickel-titanium files and pluggers improved portions of the root canal procedure, problems remain with respect to the irrigation, aspiration and disinfection of the canal. Presently, the irrigation solutions used to clean, disinfect, and remove debris in the canal are delivered using rigid irrigation needles. These needles are typically made of stainless steel and possess blunt ends. The distal end of the needle typically possesses slits or other structural components to ensure that the solution is distributed both axially and radially within the canal.

The rigid nature of a stainless steel irrigation syringe prevents an endodontist from reaching the bottom of a root canal with a syringe. Accordingly, an endodontist cannot directly irrigate the distal end of the root canal adjacent the apical foramina or a large portion of the complex network of fine lateral fissures, tubules and canals that extend from the main canal. The bottom of the root canal and the fine web of fissures may act as a breeding ground for bacteria that may later lead to a serious infection resulting in failure of the endodontic treatment and loss of the tooth. Using current syringes, the endodontist must try to force the solution, through exertion of hydraulic pressure, to the bottom of the canal and into the fine fissures and canals or make geometric adjustments to the insertion angle. If too much pressure is exerted, the solution may exit the root canal seriously damaging underlying tissue. Geometric adjustments to the insertion angle to extend the insertion distance may damage the crown. In short, complete irrigation and proper disinfection of the canal cannot be ensured using known instruments.

Accordingly, a need exists for an endodontic instrument that allows an endodontist to inject irrigation, disinfecting, and debris removal solutions adjacent the distal end of a root canal. Such an instrument must also be compatible with the physical and geometric constraints imposed by structure of the root canal.

OBJECT AND SUMMARY OF THE INVENTION

An object of the present invention is to provide an improved endodontic instrument and method for use in root canal therapy. A further object of the invention is to provide an improved endodontic instrument and method for irrigating and disinfecting root canals during endodontic procedures. A still further object of the invention is to provide an improved endodontic instrument and method that allows for the injection of irrigating and disinfecting solutions at the distal end of a root canal adjacent the apical foramina.

The above and other objects and advantages of the present invention are achieved in the embodiments illustrated herein by the provision of an endodontic instrument adapted for use in performing root canal therapy on a tooth. The endodontic instrument according to the invention is particularly useful for irrigating a root canal possessing a non-linear central axis. In one embodiment, the endodontic instrument according to the invention comprises an elongate shank having a first end and an opposite second end and an enclosed axial channel extending the length of the shank for providing fluid communication between the first end and the second end. The enclosed axial channel delivers fluids to areas external to the second end of the shank (i.e., the wall of a root canal). The instrument also comprises at least one radial orifice positioned adjacent the second end for providing radial dispersion of fluid from the orifice. The instrument is further defined as possessing a shank having a flexibility sufficient to substantially traverse the entire length of a root canal having a non-linear central axis and position the second end of the shank adjacent the distal end of the curved root canal and the apical foramina.

In a further embodiment, the invention is a method for irrigating a root canal possessing a non-linear central axis. The method according to the invention comprises transferring a fluid by way of a needle from the crown of the tooth along the non-linear central axis of a root canal to a discharge point adjacent the apical foramina. Thereafter, the method comprises discharging a fluid from an orifice at the distal end of the needle such that a portion of the fluid is discharged along a vector that is substantially perpendicular to the openings of the side canals and tubules extending from the main root canal and adjacent the apical foramina.

BRIEF DESCRIPTION OF THE DRAWINGS

This invention may be better understood and its numerous objects and advantages will become apparent to those skilled in the art by reference to the accompanying drawings in which:

FIG. 1 is a perspective view of an endodontic irrigation needle in accordance with the invention.

FIG. 2 is a schematic representation of the irrigation of a root canal in accordance with one embodiment of the invention.

DETAILED DESCRIPTION

Figure 3:
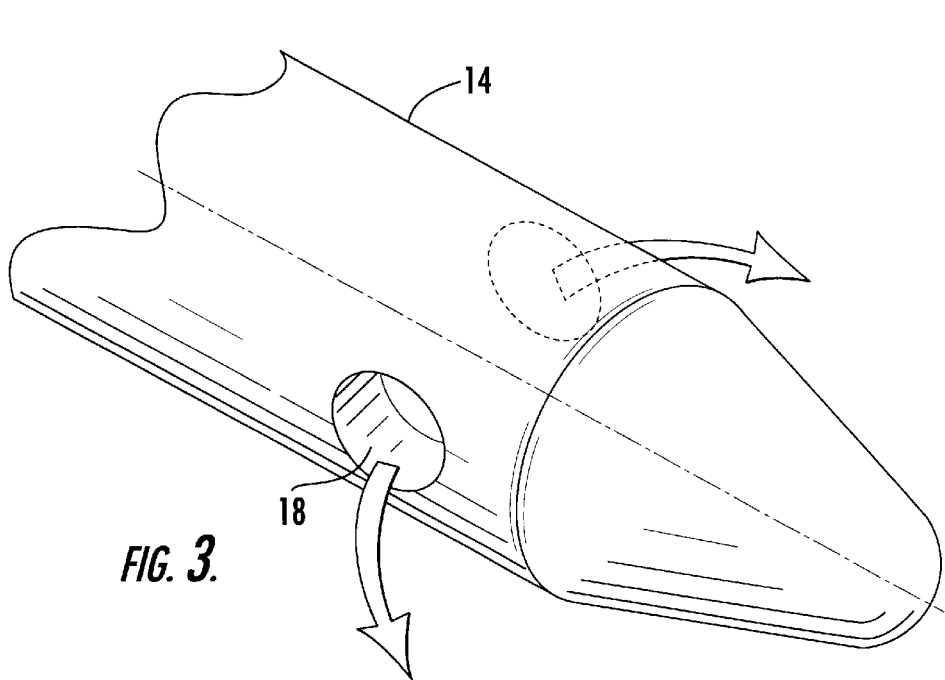
FIG. 3 is a perspective view of one end of a needle.

One embodiment of the claimed invention is an endodontic instrument adapted for use in performing root canal therapy on a tooth. The claimed invention is particularly useful in irrigating a root canal possessing a non-linear central axis. Referring now to FIG. 1, the endodontic instrument comprises an elongate shank 10 having a first end 12 and an opposite second end 14. As shown in FIG. 3, the second end of the shank 14 is preferably rounded or blunt to prevent unwanted breaches of the wall of the root canal. The shape of the second end of the shank, however, may be angled or pointed if desired or needed for a particular application.

Figure 5:
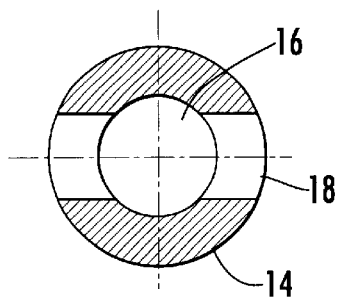
FIG. 5 is a cross-sectional view of a distal end of a needle.
Figure 4:
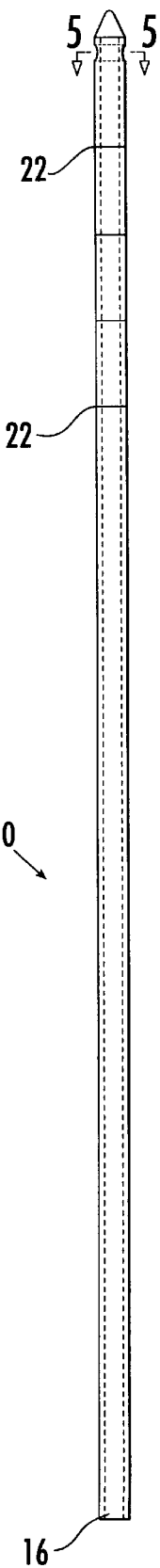
FIG. 4 is a cross-sectional view of a needle.
Figures 6, 7:
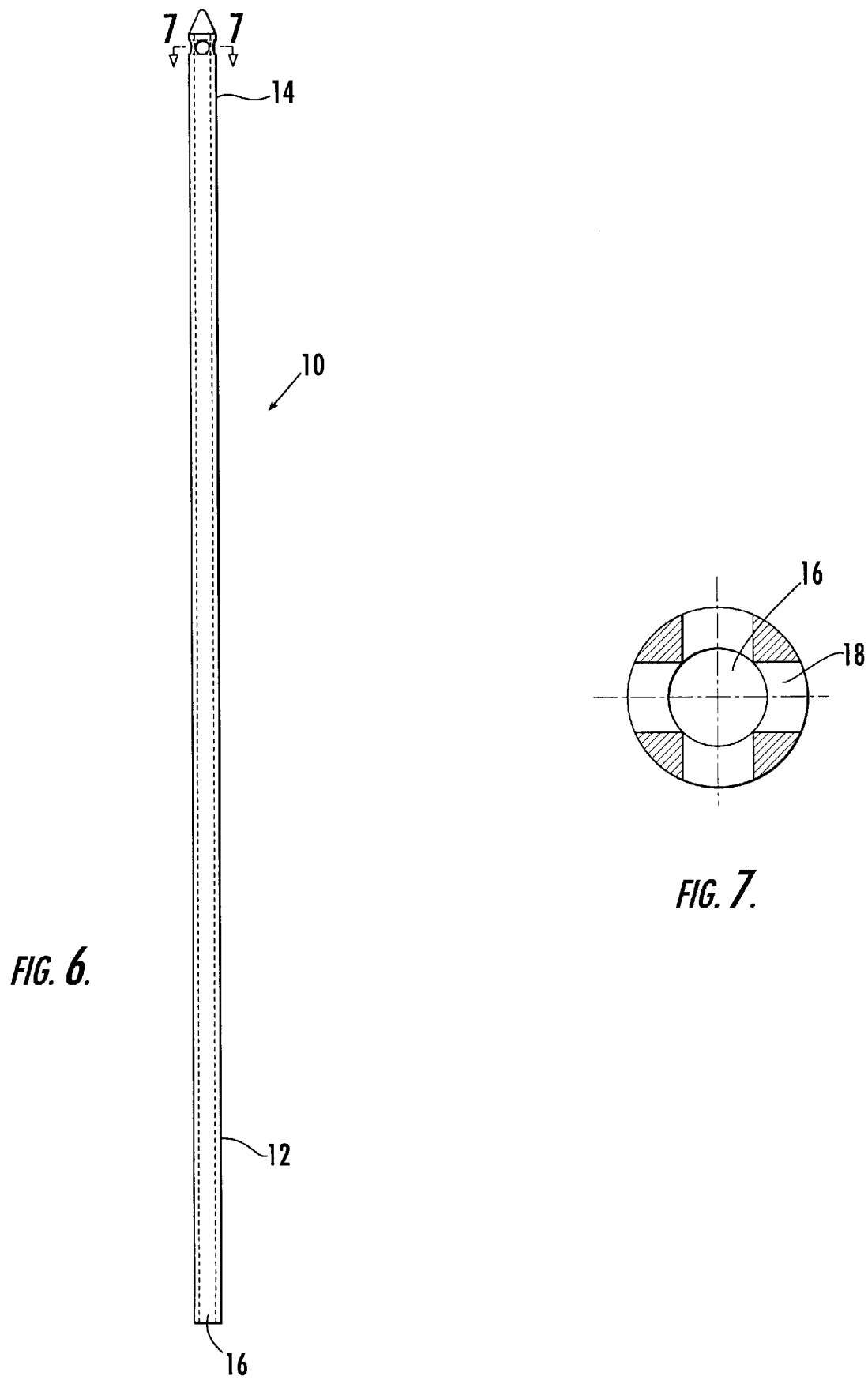
FIG. 6 is a cross-sectional view of a needle.
FIG. 7 is a cross-sectional view of a distal end of a needle.

An enclosed axial channel or lumen 16, such as those utilized in hypodermic needles, extends the length of the shank. An enclosed axial channel or lumen 16 is shown schematically by dotted lines in FIG. 4 and in cross-section in FIGS. 5 and 7. The enclosed axial channel 16 provides fluid communication (i.e., a pathway for fluid transfer) between the first end 12 of the shank and the second end 14 of the shank and to areas external to the second end of the shank (i.e., the root canal).

At least one radial orifice 18 is positioned adjacent the second end 14 of the shank. As used herein, the term "radial orifice" is utilized to convey the fact that the instrument according to the invention delivers fluid in a manner distinctly different from traditional needles or syringes used in other medical procedures. Whereas most needles eject fluid along a path aligned with the needle's elongate axis, the instrument according to the invention is designed to eject fluid or cause fluid to eject at an angle oblique from or perpendicular to the shank's elongate axis as shown in FIG. 3. The radial dispersion of the fluid is accomplished by creating at least one orifice having at least one cross-sectional plane that is oblique or parallel to the elongate axis of the shank. Such orifices are familiar to those skilled in the art. Further, it is to be understood that the orifices shown in the figures are representative and are not intended to limit the scope of the invention.

Referring now to FIGS. 3–7, the shank 10 possesses several orifices 18 adjacent the second end 14 of the shank. Each orifice 18 is a hole situated along the perimeter of the shank 10. Each orifice 18 or hole possesses at least one cross-sectional plane that is oblique or parallel to the elongate axis of the shank.

Figures 8, 9:
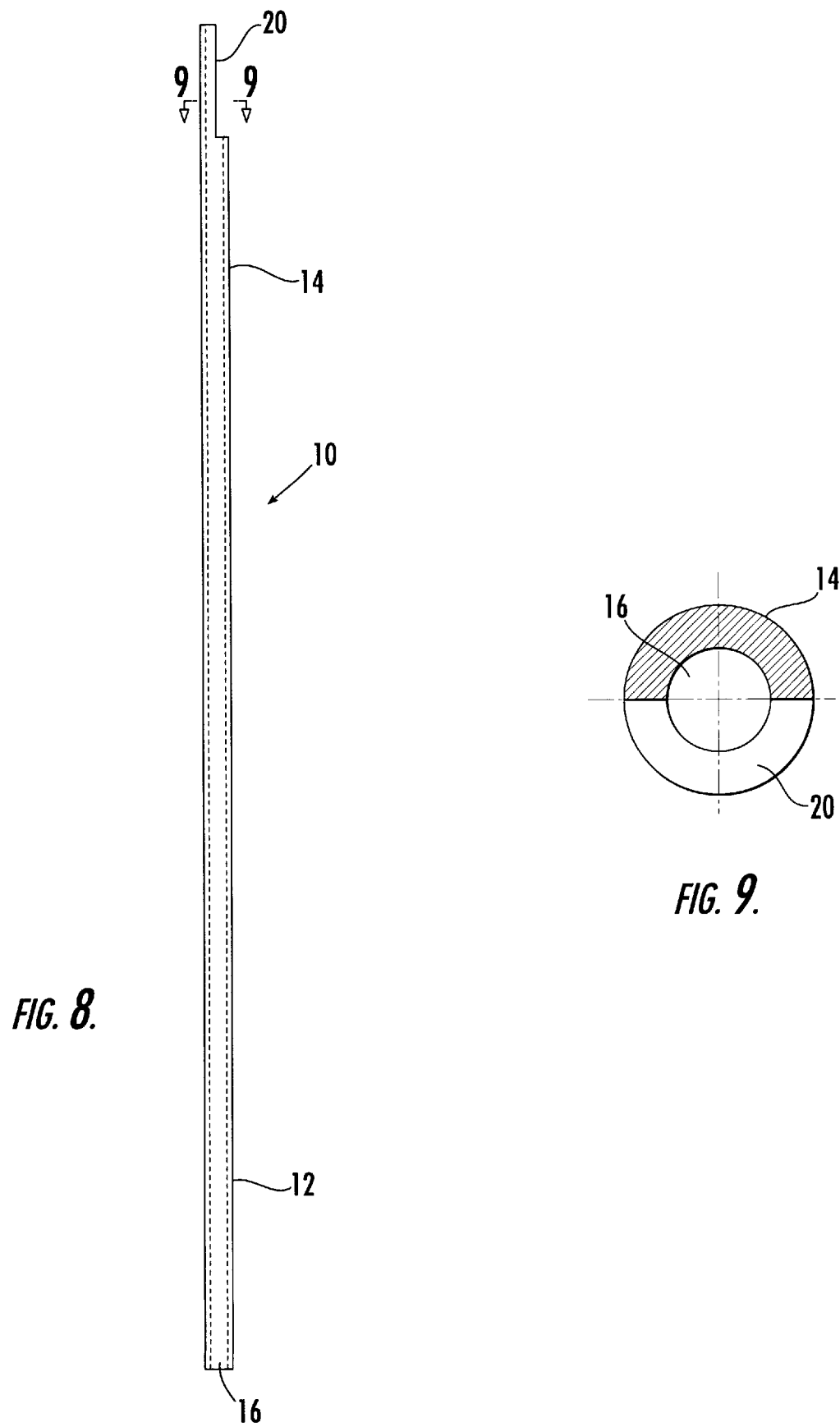
FIG. 8 is a cross-sectional view of a needle.
FIG. 9 is a cross-sectional view of a distal end of a needle.

Alternatively, radial dispersion is accomplished by removing a portion of the shank's wall at the terminus of the second end 14 of the shank as shown in FIG. 8. The removal of the wall creates a semi-cylindrical opening 20 at the terminus of the second end 14. The semi-cylindrical opening allows at least a portion of the exiting fluid to exit at an angle oblique to the shank's elongate axis.

The dispersion of the fluid at an angle oblique or perpendicular to the shank's elongate axis is important for a number of reasons. For example, a fine web of small canals and tubules extends in all directions from the main root canal. Known needles are incapable of ejecting irrigating or disinfecting fluid directly at the wall of the root canal at all points along the curve of the canal. Currently, endodontists must create a hydraulic head in the root canal to force the fluid to the bottom of the canal and into the smaller branch canals. As discussed previously, creating excessive pressures inside the root canal risks damaging the root canal and should be avoided.

Referring again to FIG. 4, the shank 10 preferably possesses spaced apart depth calibration markings 22 positioned at intervals along the length of the shank. Such depth calibration markings enable the endodontist to determine the depth reached during the procedure. Such markings are well known in the art and may vary in size or spacing.

Referring now to FIG. 2, the shank 10 substantially traverses the entire length of a root canal having a non-linear central axis to a point adjacent the distal end of the canal and the apical foramina 11. The shank 10 should be flexible and possess shape memory sufficient to return to its original position after bending. Presently, alloys of nickel and titanium are best suited for the invention's purposes. In particular, alloys comprising at least about 30% titanium and at least about 50% nickel are preferred. Polymer chemistry may soon provide materials suitable for use as a shank as described by the invention and accordingly are within the scope of the invention.

The majority of the shanks utilized in accordance with the invention will have a uniform diameter from the first end 12 to the second end 14. Certain applications, however, may require a tapered shank. Accordingly, the invention encompasses instruments utilizing a shank that is tapered at an included angle of between about ½ and about 5 degrees. In other words, the shank tapers from a thicker first end 12 to a thinner second end 14.

The instrument according to the invention further comprises a coupling for establishing fluid communication between the needle and a fluid reservoir. Couplings for attaching needles to syringes are well known to those skilled in the art.

Most medical syringes may be used with a variety of interchangeable needles of varying diameter and length, as envisioned by the apparatus according to the invention. In most instances, needles are attached to syringes using a Luer coupling or connector. Luer couplings typically come in two forms, both of which are attached and detached by application of a simple mechanical force. One form is a simple conical device which accepts the needle base. This version is often described as a Luer tip. To detach the needle, one simply pulls it off by applying a linear force.

The other type is often described as a Luer lock. The Luer lock has a simple screw thread locking mechanism that permits the base of the needle to be screwed onto the syringe upon the application of a torque so that it cannot be pulled without unscrewing. Such connectors are well known to those skilled in the art and are the subject of numerous patents such as U.S. Pat. No. 6,033,386 to Novacek et al.; U.S. Pat. No. 5,984,373 to Fitoussi et al.; U.S. Pat. No. 5,047,021 to Utterbery; and U.S. Pat. No. 4,452,473 to Ruschlee.

Although traditional syringe needle couplings may be utilized in the practice of the invention, in many instances such couplings are not practical or even suitable. For example, a patient's mouth opening is limited and it may be impossible for an endodontist to reach a tooth, such as a molar, with a needle attached to a syringe using a traditional linear coupling.

Currently, endodontists address this problem by bending the tips of the stainless steel needles used for irrigation. Typically, a 45°–90° bend is utilized. This functionally transforms the upper portion of the needle into an extension that allows the lower portion of the needle to reach a tooth and enter it through the crown. The flexible nature of the needle utilized in the practice of the invention makes this option impracticable. Accordingly, the invention may utilize an extended and angled coupling that creates a suitable angle between the fluid reservoir and the needle. An example of such a coupling is shown in FIGS. 2 and 10.

Figure 10:
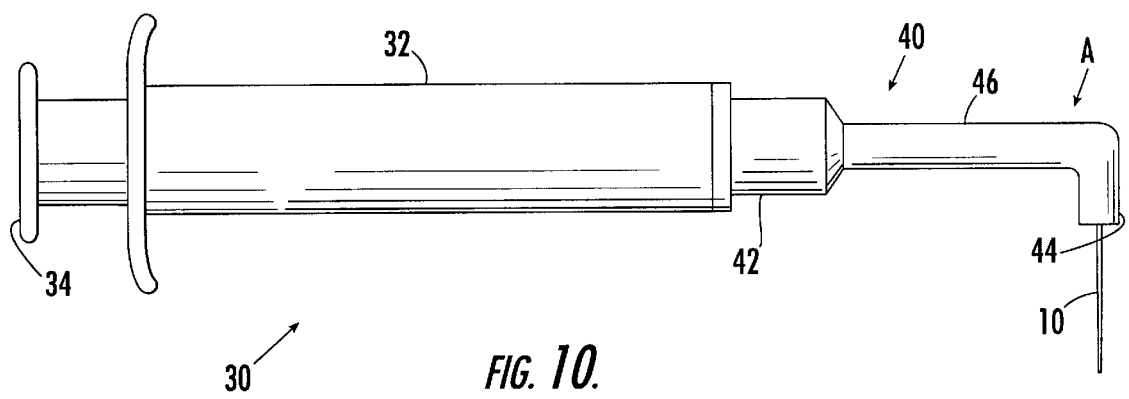
FIG. 10 is a side view of a syringe according to the invention.

Referring now to FIG. 10, a connector 40, preferably a Luer type connector, is shown. Typically, these connectors are formed of polymers. The connector 40 possesses a first end 42 and a second end 44 and an intermediate portion 46 positioned between the first end 42 and the second end 44. The intermediate portion 46 is elongate and forms an angle, identified generally at A in FIG. 10, between the first end 42 and the second end 44. The connector also possesses a lumen (not shown) extending its length providing fluid communication between the first end 42 and the second end 44.

The embodiment shown in FIG. 10 is designed such that the needle is fixably attached at the second end 44 while the first end 42 is removably attached to the distal end of a syringe or fluid reservoir as shown in FIGS. 2 and 10 and discussed below. In this design, the distance between the angle A and the first end 42 functions as an extension allowing the endodontist to reach and enter teeth easily and comfortably both for the endodontist and patient.

A further embodiment of the apparatus according to the invention encompasses an endodontic irrigation syringe of the type shown in FIG. 10. The syringe 30 according to the invention comprises a reservoir for retaining irrigation or disinfecting fluid and means for dispensing a fluid from the reservoir. Typically, the function of the reservoir and means for dispensing are provided by a hollow, axially elongated barrel or tube 32 and plunger 34 combination commonly associated with hypodermic needles and other such medical devices. The syringe 30 further comprises a shank 10 of the type previously discussed that is in fluid communication with the fluid reservoir, fluid communication is accomplished by means of the connector 40 that is removably attached to the distal end of the barrel 32. The connector 40 is of the type previously described.

A still further embodiment of the invention encompasses a method for irrigating a root canal possessing a non-linear central axis. The method comprises inserting an elongate, hollow and flexible shank or needle of the type previously discussed into a root canal along a path that generally follows the non-linear central axis of the root canal. In this manner the distal end of the needle and its orifices are positioned adjacent the distal end of the root canal and the apical foramina.

The insertion of the shank is followed by transferring a fluid, by way of the needle, from the crown of the tooth along the non-linear central axis of the root canal to a discharge point adjacent the apical foramina. Thereafter, the fluid is discharged from an orifice at the distal end of the needle such that a portion of the fluid is discharged along a vector that is substantially perpendicular to the openings of the side canals and tubules extending from the main root canal and adjacent the apical foramina. This manner of irrigating and disinfecting provides a more direct application of fluid to the bottom of the root canal and the smaller accessory canals that branch from the main canal thus improving the effectiveness of the overall procedure.

The invention has been described in detail, with reference to certain preferred embodiments, in order to enable the reader to practice the invention without undue experimentation. However, a person having ordinary skill in the art will readily recognize that many of the components and parameters may be varied or modified to a certain extent without departing from the scope and spirit of the invention. Furthermore, titles, headings, or the like are provided to enhance the reader's comprehension of this document, and should not be read as limiting the scope of the present invention. Accordingly, only the following claims and reasonable extensions and equivalents define the intellectual property rights to the invention.

That which is claimed is:

1. An endodontic instrument adapted for use in performing root canal therapy on a tooth and that is particularly useful for irrigating a root canal possessing a non-linear central axis, the instrument comprising:

an elongate shank having a first end and an opposite second end wherein said shank is a metallic alloy comprising at least about 30% titanium and at least about 50% nickel;

an enclosed axial channel extending the length of the shank for providing fluid communication between said first end and said second end for delivering fluids to areas external to said second end of said shank; and at least one radial orifice positioned adjacent said second end for providing radial dispersion of fluid from said orifice;

said shank being sufficiently flexible to substantially traverse the entire length of a root canal having a non-linear central axis and position said second end of said shank adjacent the distal end of the curved root canal and the apical foramina.

2. The endodontic instrument of claim 1 wherein said second end of the shank comprises a blunt end surface.

3. The endodontic instrument of claim 1 wherein said orifice comprises at least one hole situated along the perimeter of said shank.

4. The endodontic instrument of claim 1 wherein said orifice comprises a semi-cylindrical structure at the terminus of said second end of said shank.

5. The endodontic instrument of claim 1 further comprising a plurality of axially spaced apart depth calibration markings positioned along the shank.

6. The endodontic instrument of claim 1 wherein the shank of said instrument is tapered at an included angle of between about ½ and about 5 degrees.

7. The endodontic instrument of claim 1 further comprising a fitting mounted at said first end of the shank, said fitting for establishing fluid communication between said enclosed axial channel and a fluid reservoir.

8. The endodontic instrument of claim 7 further comprising a fluid reservoir in fluid communication with said enclosed axial channel.

9. An endodontic irrigation syringe comprising:
   a reservoir for retaining a fluid;
   a needle in fluid communication with said reservoir, said needle comprising an elongate shank having a first end and an opposite second end and an enclosed axial channel extending the length of the shank for providing fluid communication between said reservoir and said second end and for delivering fluids to areas external to said second end of said shank, said shank being sufficiently flexible to substantially traverse the entire length of a root canal having a non-linear central axis and position said second end of said shank adjacent the distal end of the curved root canal and the apical foramina, and wherein said shank is a metallic alloy comprising at least about 30% titanium and at least about 50% nickel;
   at least one radial orifice positioned adjacent said second end for providing radial dispersion of fluid from said orifice; and
   means for dispensing a fluid from said reservoir to said channel of said needle.

10. The endodontic irrigation syringe of claim 9 wherein said second end of the shank comprises a blunt end surface.

11. The endodontic irrigation syringe of claim 9 wherein said orifice comprises at least one hole situated along the perimeter of said shank.

12. The endodontic irrigation syringe of claim 9 wherein said orifice comprises a semi-cylindrical structure at the terminus of said second end of said shank positioned along the shank.

13. The endodontic irrigation syringe of claim 9 wherein the shank of said needle is tapered at an included angle of between about ½ and about 5 degrees.

14. A method for irrigating a root canal possessing a non-linear central axis, the method comprising:
   transferring a fluid by way of a needle comprising at least about 30% titanium and at least about 50% nickel and extending from the crown of the tooth along the non-linear central axis of the root canal to a discharge point adjacent the apical foramina and thereafter discharging the fluid from an orifice at the distal end of the needle such that a portion of the fluid is discharged substantially perpendicularly to the openings of the side canals and tubules extending from the main root canal and adjacent the apical foramina.

15. A method according to claim 14 in which the fluid comprises at least one fluid selected from the group consisting of disinfecting agents and chelating agents.

16. A method according to claim 15 wherein the disinfecting agent is sodium hypochlorite and the chelating agent is EDTA.

17. A method according to claim 14 wherein said orifice comprises a semi-cylindrical structure at the terminus of the distal end of the needle.

18. A method according to claim 14 further comprising adjusting the depth of insertion by measuring a plurality of axially spaced apart depth calibration markings positioned along the needle.

19. A method according to claim 14 wherein the needle is tapered at an included angle of between about ½ and about 5 degrees.

20. A method for irrigating the distal end of a root canal possessing a non-linear central axis, the method comprising:
   inserting an elongate, hollow and flexible shank, comprising at least about 30% titanium and at least about 50% nickel and having a first end and an opposite second end, into a root canal along a path that generally follows the non-linear central axis of the root canal and positioning the second end of the shank adjacent the distal end of the root canal and the apical foramina; and
   injecting an irrigation fluid into the distal end of the root canal through an orifice adjacent the second end of the shank whereby at least a portion of the irrigation fluid impacts the sideway of the root canal at an angle that is substantially perpendicular to the central axis of the root canal.

21. A method according to claim 20 in which the irrigating fluid is selected from the group comprising disinfecting agents and chelating agents.

22. A method according to claim 20 wherein said second end of the shank comprises a blunt end surface.

23. A method according to claim 20 wherein said orifice comprises at least one hole situated along the perimeter of the shank.

24. A method according to claim 20 wherein said orifice comprises a semi-cylindrical structure at the terminus of the second end of the shank.

25. A method according to claim 20 further comprising adjusting the depth of insertion by measuring a plurality of axially spaced apart depth calibration markings positioned along the shank.

26. A method according to claim 20 wherein the shank is tapered at an included angle of between about ½ and about 5 degrees.

27. A syringe comprising:
   a hollow, axially elongated barrel;
   a needle;
   a removable connector attached to said barrel adjacent a distal end thereof said connector comprising a first end removably attached to said distal end of said barrel and a second end attached to said needle, said first and second ends being separated by an intermediate portion, said intermediate portion being non-linear and forming an angle between said first end and said second end, said connector further comprising a lumen extending the length and thereof and providing fluid communication between said barrel and said needle;
   said needle comprising an elongate shank comprising at least about 30% titanium and at least about 50% nickel and having a first end and an opposite second end and an enclosed axial channel extending the length of the shank for providing fluid communication between said barrel and said second end of said shank and for delivering fluids to areas external to said second end of said shank, said shank being sufficiently flexible to substantially traverse the entire length of a root canal having a non-linear central axis and position said second end of said shank adjacent the distal end of the curved root canal and the apical foramina;

at least one radial orifice positioned adjacent said second end of said shank for providing radial dispersion of fluid from said orifice; and means for dispensing a fluid from said barrel to said channel of said needle.

28. The syringe of claim 27 wherein said second end of said shank comprises a blunt end surface.

29. The syringe of claim 27 wherein said connector is removable from said barrel in response to the application of a torque.

30. The syringe of claim 27 wherein said connector is removable from said barrel in response to the application of a linear force.

31. The syringe of claim 27 wherein said angle is selected from the group consisting of obtuse and right angles.

* * * * *

UNITED STATES PATENT AND TRADEMARK OFFICE
CERTIFICATE OF CORRECTION

PATENT NO. : 6,638,064 B1  Page 1 of 1
DATED : October 28, 2003
INVENTOR(S) : Nance It is certified that error appears in the above-identified patent and that said Letters Patent is hereby corrected as shown below:

<u>Column 8,</u>
Line 28, "sideway" should read -- sidewall --;
Line 61, after "length" cancel "and".

Signed and Sealed this

Thirteenth Day of January, 2004

JON W. DUDAS
*Acting Director of the United States Patent and Trademark Office*